(12) United States Patent
Borrell

(10) Patent No.: US 11,938,107 B1
(45) Date of Patent: Mar. 26, 2024

(54) PRODUCTION PROCEDURE FOR ALQUERNAT CONEB, A FUNCTIONAL FEED BASED ON ALLIIN, CARVACROL, CIMENOL AND INULIN FROM VEGETABLE EXTRACTS, TO BE USED IN THE PREVENTION OF PARASITIC INFESTATIONS IN POULTRY FEED

(71) Applicant: BIOVET, S.A., Cambrils (ES)

(72) Inventor: Jaime Valls Borrell, Tarragona (ES)

(73) Assignee: BIOVET, S.A., Cambrils (ES)

( * ) Notice: Subject to any disclaimer, the term of this patent is extended or adjusted under 35 U.S.C. 154(b) by 0 days.

(21) Appl. No.: 16/120,205

(22) Filed: Aug. 31, 2018

(51) Int. Cl.

| | |
|---|---|
| A61K 36/00 | (2006.01) |
| A23K 10/30 | (2016.01) |
| A23K 40/10 | (2016.01) |
| A23K 50/75 | (2016.01) |
| A61K 9/00 | (2006.01) |
| A61K 31/05 | (2006.01) |
| A61K 31/198 | (2006.01) |
| A61K 31/733 | (2006.01) |
| A61K 36/28 | (2006.01) |
| A61K 36/53 | (2006.01) |
| A61K 36/88 | (2006.01) |
| A61K 47/44 | (2017.01) |
| A61P 33/00 | (2006.01) |

(52) U.S. Cl.
CPC ............ *A61K 31/198* (2013.01); *A23K 10/30* (2016.05); *A23K 40/10* (2016.05); *A23K 50/75* (2016.05); *A61K 9/0056* (2013.01); *A61K 31/05* (2013.01); *A61K 31/733* (2013.01); *A61K 36/28* (2013.01); *A61K 36/53* (2013.01); *A61K 36/88* (2013.01); *A61K 47/44* (2013.01); *A61P 33/00* (2018.01)

(58) Field of Classification Search
None
See application file for complete search history.

(56) References Cited

U.S. PATENT DOCUMENTS

2006/0216251 A1* 9/2006 Morariu ................. A61K 8/606 424/59
2017/0000755 A1* 1/2017 Arhancet ............. A23K 20/189
2017/0143022 A1* 5/2017 Wicker .................. A23L 27/20

OTHER PUBLICATIONS

Baser et al. (2008) Current Pharmaceutical Design, 14: 3106-3120. (Year: 2008).*
Cervato et al. (2000) J. Food Biochem. 24: 453-465. (Year: 2000).*
Chung (2006) J. Med. Food 9 (2): 2005-213. (Year: 2006).*
El-Nekeety et al. (2011) Toxicon 57: 984-991. (Year: 2011).*
Fachini-Queiroz et al. (2012) Evidence-Based Comlementary and Alternative Medicine, vol. 2012, Article ID 657026, 10 pages. (Year: 2012).*
Lopez-Molina et al. (2005) Phytochemistry 66: 1476-1484. (Year: 2005).*
Martinez-Romero et al. (2007) Inter. J. Food Microbiol. 115: 144-148. (Year: 2007).*

* cited by examiner

*Primary Examiner* — Russell G Fiebig
(74) *Attorney, Agent, or Firm* — MICHAEL J. BOOTCHECK, LLC; Michael J. Bootcheck

(57) ABSTRACT

A production procedure for procedure for Alquernat Coneb, a poultry feed (broiler breeders and turkeys) based on alliin, carvacrol, cimenol and inulin from vegetable extracts, and its use in the prevention of parasitic infestations.

1 Claim, 7 Drawing Sheets

PRODUCTION PROCEDURE FOR ALQUERNAT CONEB, A FUNCTIONAL FEED BASED ON ALLIIN, CARVACROL, CIMENOL AND INULIN FROM VEGETABLE EXTRACTS, TO BE USED IN THE PREVENTION OF PARASITIC INFESTATIONS IN POULTRY FEED

FIELD OF THE INVENTION

This invention relates to the obtention of aromatic compounds extracted from *Allium sativum, Origanum vulgare, Thymus vulgaris* and *Cynara scolymus* and which stimulate local immune response and the regeneration of the enterocytes. The immune response breaks the cycle of parasites, eliminating them from the epithelial cells. In addition, it controls pathogenic growth in the gut and improves intestinal absorption.

The final product obtained acts as intestinal optimizer and conditioner of the intestinal mucosa, improving digestive well-being of the animals and the productive parameters of the farms.

Additionally, a procedure has been developed for obtaining Alquernat Coneb in powder, a product easy to preserve and administer, but at the same time with the nutritional contents of a fresh product.

BACKGROUND OF THE INVENTION

The use of botanical species is widely known since antiquity. New insights in pronutrients are allowing to study which active principles contained in plants are, what its chemical structure and which routes are followed to achieve the physiological action for which they are intended.

Many intestinal protozoa as *Coccidia, Cochlosoma* or *Histomonas* among others, colonize the intestinal mucosa of broiler breeders and turkeys. This colonization causes an immune response in animals, which triggers a significant reduction in productive parameters and an increase in susceptibility to other intestinal diseases.

What is needed is a product or process to address the foregoing problems or at least to provide the public with a useful choice. Further aspects of the present invention will become apparent from the ensuing description which is given by way of example only.

DETAILED DESCRIPTION OF THE INVENTION

Figure 1:
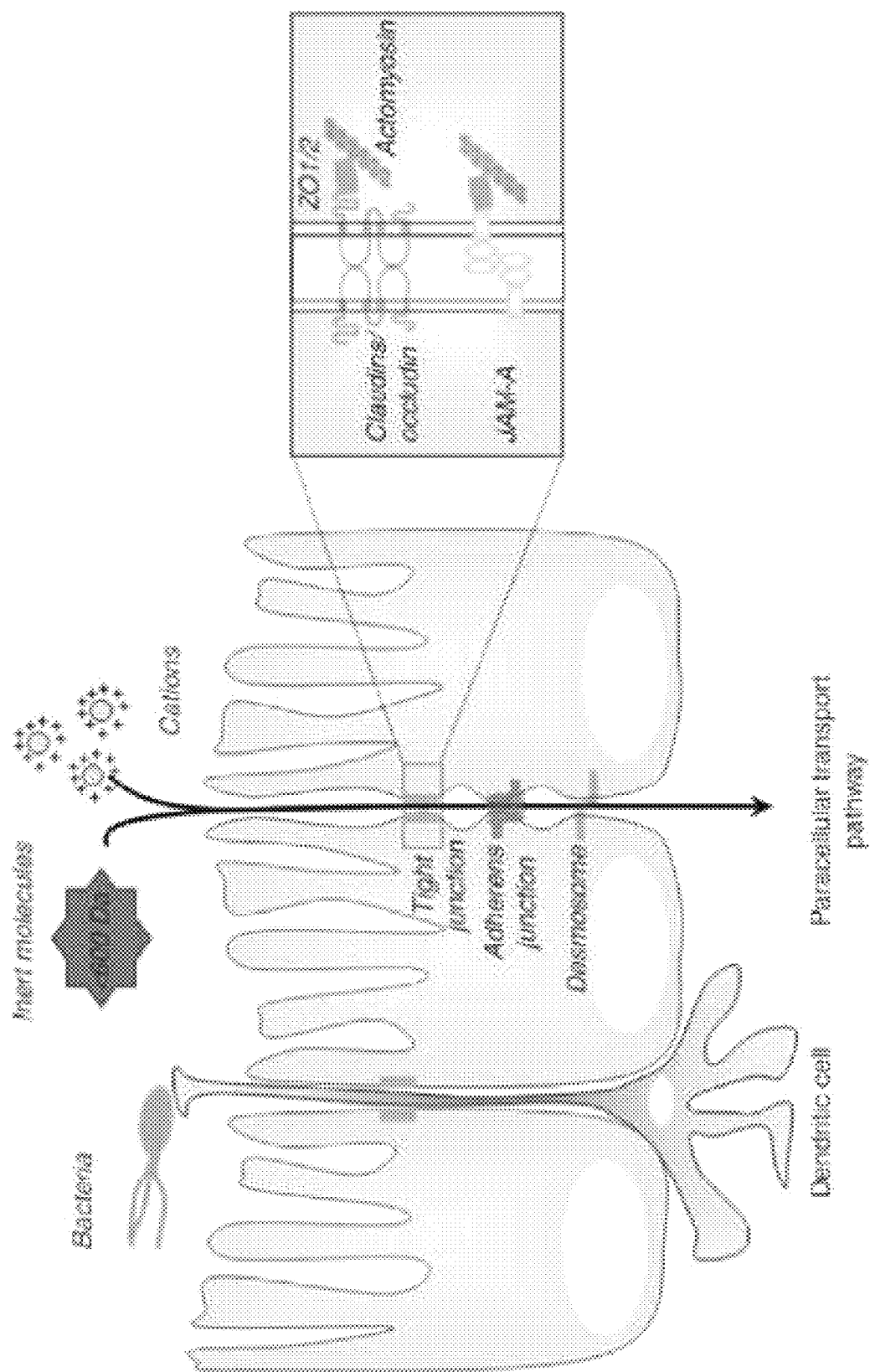
FIG. 1 is a graphical illustration of the immune system.

To promote an understanding of the principles of the present invention, descriptions of specific embodiments of the invention follow and specific language is used to describe the specific embodiments. It will nevertheless be understood that no limitation of the scope of the invention is intended by the use of specific language. Alterations, further modifications, and such further applications of the principles of the present invention discussed are contemplated as would normally occur to one ordinarily skilled in the art to which the invention pertains.

1.1 *Allium sativum* Extract Providing Alliin

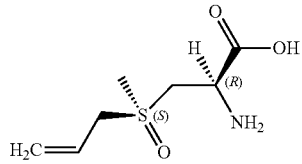

The underground bulb of *Allium sativum* contains numerous active components, among which sulfur compounds are shown off. If the bulb is intact and fresh, the major compound is S-Allyl-L-cysteine sulfoxide or Alliin. This is an unstable compound which is hydrolyzed by action of the alliinase enzyme, which is also present in the bulb, becoming allicin. Allicin is also a high-volatile compound.

Alliin is present in cytosol, which is also the substrate of alliinase enzyme found in separate vacuoles. When garlic is crushed, the vacuoles containing the enzyme are broken and the reaction takes place with the alliin to form an intermediate which condenses to give allicin.

The present invention relates to the production of *Allium sativum* extract which keeps the content of alliin and alliinase intact, so that the biochemical process of conversion of alliin in its derivatives occurs when the product comes into contact with saliva, whose conditions are suitable for activating the enzyme for the hydrolysis of alliinase. So that the benefits of the pronutrients contained in *Allium sativum* extract are maximum, because the concentration is without losses. This would improve the offer, with wide application in animal feed industry, based in authorized substances as feed additives.

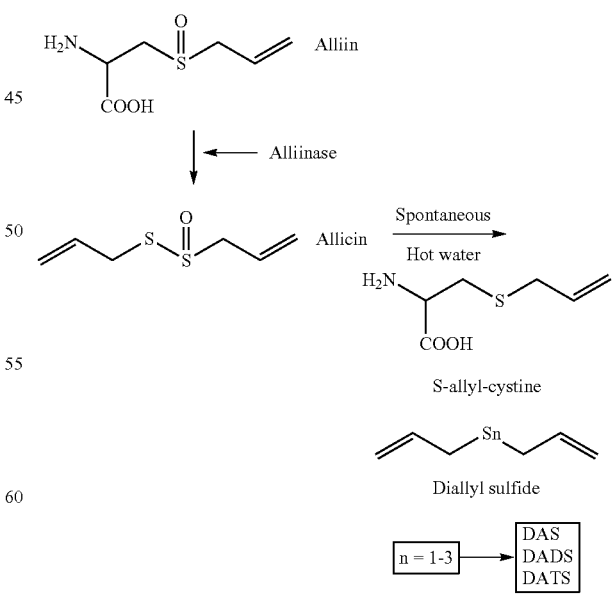

The above formulas illustrate the structure of one of the major compounds in garlic and its derivatives. DAS: Diallyl sulfide; DADS: Diallyl disulfide; DATS: Diallyl trisulfide

1.2 Origanum vulgare Extract Providing Carvacrol

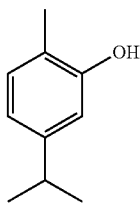

Carvacrol inhibits the growth of various strains of bacteria and eliminates a high number of pathogens that would produce harmful toxins in the intestine. Some of these pathogens are associated with gastroenteritis, hemorrhagic diarrhea, renal failure, among others.

Carvacrol damages the integrity of the cell wall of bacteria. It is particularly interesting, since it has very little or little interaction with the probiotic flora of the intestine. At concentration in which it inhibits the growth of pathogenic bacteria between 97 and 100%, carvacrol only affects probiotic bacteria between 3 and 5%.

1.3 Thymus vulgaris Providing Cimenol

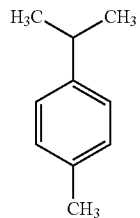

Cimenol ring has a bactericidal, fungicidal and preservative function, and is naturally present in many botanical species.

The application of cimenol ring as preservative of raw materials and feed intended for animal feed is the result of investment in R+D of Biovet, S.A., together with Universidad Politécnica de Valencia and with Universitat Rovira y Virgili in Tarragona.

In vitro test and field trials indicate that cimenol ring is effective against bacteria, yeast and fungal; gastrointestinal pathogens whose mechanism of action is:

1.3.1 Mechanism of Action in Bacteria

Cimenol ring in contact with bacteria causes the immediate release of cell contents into the medium, caused by the bacteria membrane perforation leading to cell destruction.

Cimenol ring inside the cells alters biosynthetic pathways affecting ATP (required for energy metabolism molecule), cellular pH and balance of inorganic ions.

1.3.2 Mechanism of Action in Yeast and Fungi

Appropriate concentrations of cimenol ring achieve to kill 100% of yeast and fungi in just 10 minutes of contact. Cell lysis and release of cellular content into the medium are observed. At electronic microscope, yeast and fungi are malformed and have fractures in cell walls, especially those found in proliferation phase.

Furthermore, cimenol ring inhibits ergosterol biosynthesis, the main sterol of yeast cell membrane, contributing to the destruction of the cell.

Although the materials used are known, the new manufacturing process represents an important advance, since a product with the virtues of a powder product of easy storage and administration, but at the same time with the nutritional contents of a fresh product is obtained.

1.4 Cynara scolymus Providing Inulin

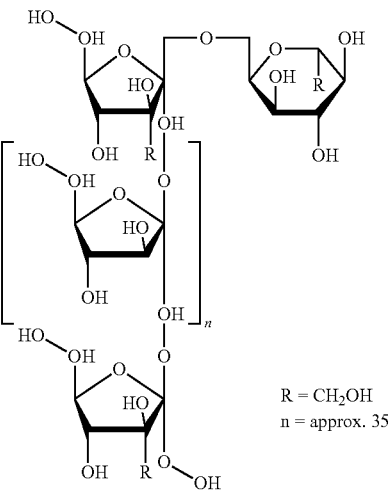

$R = CH_2OH$
$n = $ approx. 35

Inulin is a non-digestible carbohydrate generally called fructan, which is made up of several units of fructose and a terminal glucose. Inulin has several positive effects, but we basically emphasize its action in the regulation of lipid parameters and as a reinforcement of the immune response.

Inulin is part of the dietary fiber. It is moderately soluble in water and has the property of forming gels that retain a large amount of water. The subproducts of inulin metabolism increase intestinal peristalsis and facilitate the adsorption of some mineral elements.

1.5 Alliin Obtained from Allium sativum Bulbs

To obtain ecological alliin, without chemical treatments, the extraction with sunflower oil is made, to avoid the contact of the bulb with air to minimize the hydrolysis of the compound by the action of alliinase. The whole garlic cloves are introduced in sunflower oil and milling is done in an environment with negative pressure to minimize the presence of oxygen. When finished, filtration is done to remove the peels. The product contains 5% alliin.

An extraction is made to increase the concentration of alliin from this emulsion. For this, let stand for 2 hours and pour oily phase reducing its volume by half. Add an aqueous solution of 1 mM citric acid and treat the remaining emulsion with ethyl p-hydroxybenzoate in a ratio 1:5 and an emulsifier and then homogenize for 30 minutes. Thus we obtain an Allium sativum extract of an alliin purity of 16-17%.

1.6 Carvacrol Obtained from Origanum vulgare Leaves

First, oregano plant is destemmed to separate the leaves from the woody parts of the same. The leaves of Origanum vulgare are grinded and dried to facilitate the subsequent ethanolic extraction.

100 kg of dry powder of Origanum vulgare leaves were macerated with 96% ethanol at a ratio 1:3 p/v for 4 hours. A product with the consistency of an oleoresin is obtained, which will need to be adsorbed with silica gel and processed in the rotavapor at 6000 rpm for 30 minutes. 100 kg of powder product will have an efficiency of 12 kg of extract rich in carvacrol (20-22%). A standardization of the extract is performed to check the purity and richness of the same.

1.7 Cimenol Obtained from Thymus vulgaris Leaves

To obtain ecological cimenol, dried and powdered thyme leaves are pressed in cold. The obtained cake contains about 4% cimenol.

To obtain a higher concentration of active ingredient, the above cake is put in a Florence flask with enough water to achieve the suspension of the sample. This is usually a ratio of 1 kg of dried thyme in 3 liters of water.

The least sample handling is sought in order not to degrade the essential oils, which are the main source of the compound to be purified. Therefore, for the extraction of the essential oil of thyme one steam distillation is used. Due to the volatility and insolubility of the oil in water, the product will be expected to have two phases.

Subsequently an extraction is made to separate the pure essential oil with a separatory funnel. The essential oil is separated in a covered container and protected from light to prevent light decomposition. A new extraction with the aqueous portion with ether is carried out to finally separate the oil surplus remaining solubilized in this phase. The remaining traces in the ether phase are extracted of water with sodium sulphate as a desiccant. An acid-base extraction is carried out to reduce the amount of components to be separated by chromatography.

To obtain phenols, including cimenol, which are the most acid compounds in the essential oil, an acid-base extraction is done. First, oils in water solution are placed in the separatory funnel. Then, 50 ml potassium hydroxide IN are added and as phenols are the most acid compounds present in the oil, they are soluble in aqueous phase. Once the aqueous phase is isolated from the rest, it is taken to a new separatory funnel for acidification with 15 ml hydrochloric acid 2 N and 100 ml ether. Thus only phenols are obtained in ether phase.

All ether phases are combined and filtered with anhydrous sodium sulphate as a desiccant to remove traces of water. Latterly, the compound is heat in a water bath to evaporate the ether and obtained isolated phenols. This oil is absorbed with bentonite, which allows a user to get a product to a fine powder with 18-20% of cimenol. A standardization of the extract is performed to check the purity and richness of the same.

1.8 Inulin Obtained from Cynara scolymus External Bracts

To obtain inulin, external bracts from artichokes were freeze-dried, they were ground to fine particles and sieved with a 500 μm mesh. The sample was stored in a dry and hermetically closed recipient, protected from light until analysis.

To optimize the extraction and obtain a higher concentration of active principle of the artichoke bracts, pressurized liquid extraction (PLE) has been used. Although this technique requires longer times, it favors the extraction of inulin and obtaining a higher efficacy.

Dried artichoke bracts were introduced inside the stainless steel extraction cell between sand layers. Milli-Q water was used as extraction solvent and two static extraction cycles was done. Extractions were carried out under a pressure of 100 bar, and a purge of nitrogen gas of 2 min was done at the end of the extraction cycle.

The inulin concentration was calculated taking into account fructose, glucose and sucrose content of artichoke bracts extracts before after hydrolysis of inulinase. Samples are analyzed by GC.

The experimental results obtained after PLE of inulin yields from artichoke bracts are 15-20% at 75° C. and 26.7 min.

1.9 Production Procedure

Once all the active substances have been purified, after checking the concentrations by a quantitative analysis, the final product is prepared.

In this reactor 75 kg *Allium sativum* meal, 25 kg *Origanum vulgare* meal, 25 kg *Thymus vulgare* meal and 25 kg *Cynara scolymus* meal are put. Mix for 6 minutes, at which time the homogeneity of the product can be assured. At this time, the product is milled to ensure an appropriate granulometry for use in industrial facilities, which will be the final users of the product.

The animal feed obtained by the incorporation of natural ingredients from aromatic plants, is ready to be consumed with a minimum guaranteed composition of: 8.0% alliin, 3.3% carvacrol, 3.0% cimenol and 2.5% inulin. Properly packaged.

Efficacy Test

In the presence of intestinal protozoa pathogens such as *Coccidia, Cochlosoma* or *Histomonas* among others, the intestinal mucosa can be colonized. The present invention of Alquernat Coneb act by promoting the local immune system of the intestine and maintains the physiological state of the digestive tract.

Local immunity interrupts the intestinal phase of the protozoa, eliminating them from the epithelial cells. The active ingredients also stimulate the activity of intestinal polymorphonuclear cells (PMNs), in such a way that they increase the expression of IL-1, IL-12, IL-18.

The stimulation of the epithelium regeneration promotes a better digestion and nutrient absorption and allows a greater control of pathogenic microorganisms in the intestine.

Using the present invention/Aluernat Coneb, protozoa are eliminated from the intestinal mucosa, so that they cannot damage it or reach the liver or other organs.

To demonstrate the efficacy of the product, several tests have been carried out against different protozoa, which compare the use of the invention product with the methods currently used as explained above. An in vitro test demonstrates how the active ingredients of the present invention/ Alquernat Coneb protect the intestinal cells from the colonization of the parasites.

2.1 In Vitro Trial. Effect of the Present Invention/Alquernat Coneb on Tight Junctions (FITC Permeability)

Introduction: Intestinal Permeability

Tight junctions are important structures that regulate paracellular transit of macromolecules.

Changes in intestinal barrier cause a perturbation of the immune system of the inflammatory mucosa. See, e.g., FIG. 1 which is a graphical illustration of the immune system.

Experimental Design:

Cells were put in Transwell inserts, with a collagen-coated membrane, a pore size of 0.4 μm and a membrane diameter of 6.5 mm (Corning, N.Y., USA), at a density of 5×105 cell/ml and cultured for 21 days until reaching the confluence. Every three days, new cell medium was added.

Monolayers were treated with the present invention/ Alquernat Coneb 1:10000 for 90 min and then the passage of FITC (fluorescein) transit was measured from the apical 1 mg/ml) to the basoteral medium.

Figure 2:
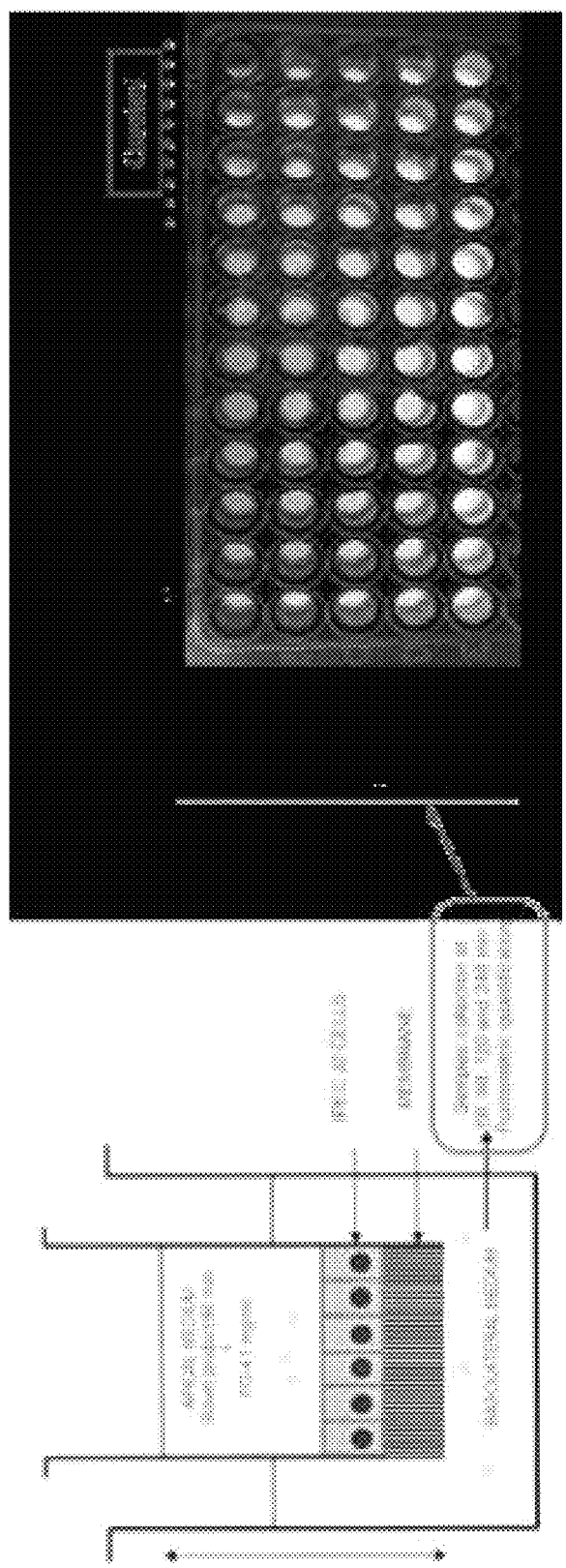
FIG. 2 is an illustration of the quantity of FITC that passed through the membrane.

Samples were collected at 30, 60, 90, 120 and 240 min and the quantity of FITC (non-absorbable) that passed through the membrane was quantified by fluorometry. See, e.g., FIG. 2 which is an illustration of the quantity of FITC (fluorescein isothyiocyanate) that passed through the membrane.

Figure 3:
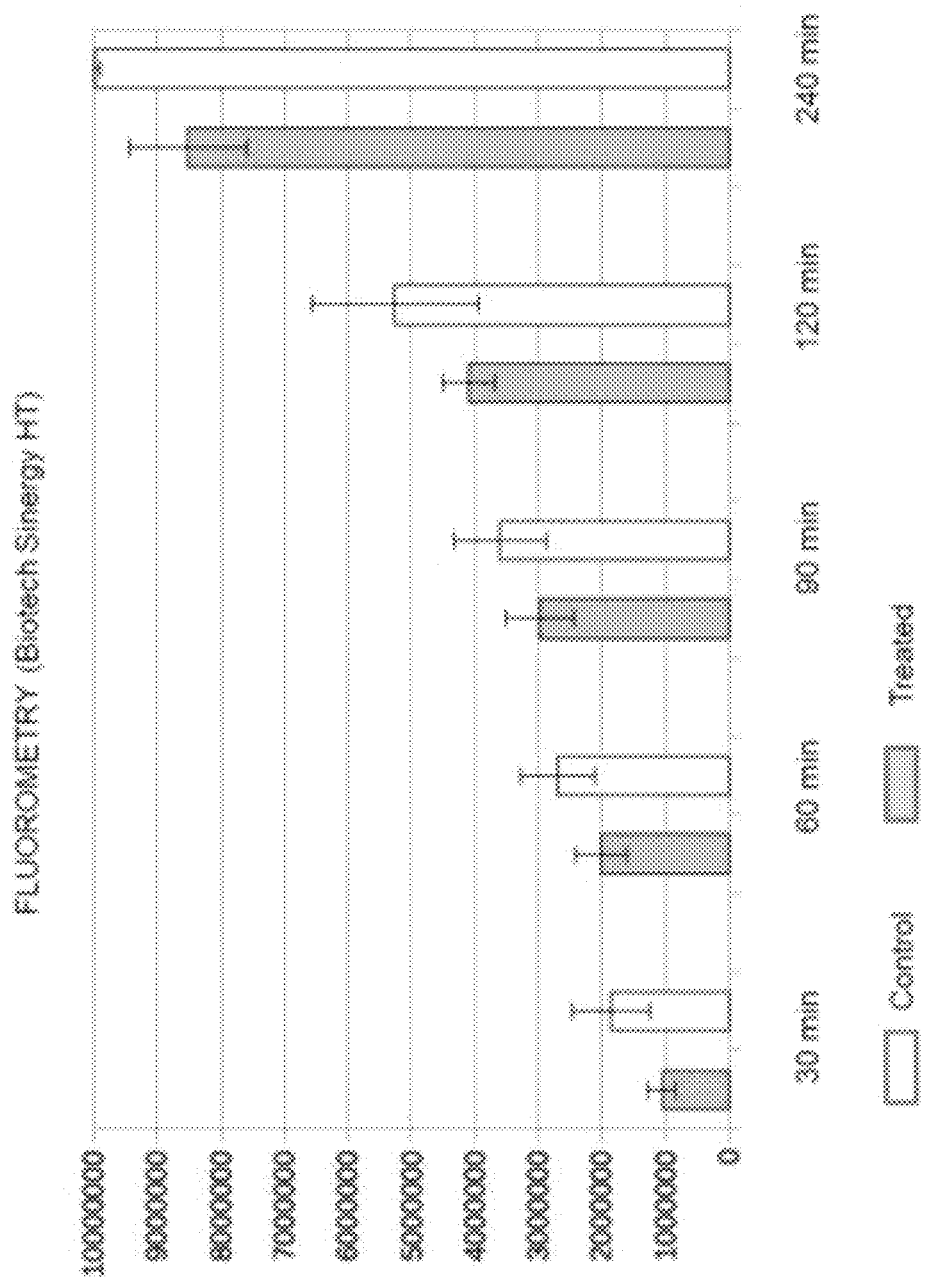
FIG. 3 is a graph illustrating the results of the fluorometry.

Results:
FIG. 3 is a graph illustrating the results of the fluorometry.

Pretreatment of polarized intestinal epithelial cells with the present invention/Alquernat Coneb reduces paracellular permeability. This results in an increase of the tight junctions in the cells treated with the present invention/Alquernat Coneb, which does not allow the passage of FITC.

Conclusions:
The active principles of the present invention/Alquernat Coneb strengthen the integrity of the intestinal barrier and protect animals against enteric pathogens, feed antigens and physicochemical tensions caused by digestive and microbial products, improving animal welfare and productive performance.

2.2 Use of the Present Invention/Alquernat Coneb in Turkeys Against Histomonas Meleagridis, Colombia, 2016

Introduction: Histomoniasis

Histomonas meleagridis is an extracellular parasite (protozoa) that causes histomoniasis, enterohepatitis or blackhead disease.

Histomoniasis in turkeys causes severe caecal and hepatic lesions leading to up to 90% mortality.

The protozoa reaches the cecum and invades caecal mucosa. Later, the parasite goes to the liver.

Experimental Design:
The clinical signs usually appear between 6 and 9 weeks of life, but can also be observed after week 10.

Feed was supplemented with the present invention/Alquernat Coneb at a dose of 1 kg/t of feed to all animals (breeders and fattening turkeys, of all ages).

Farm: Cundinamarca (Colombia)
No Birds: 170.000
Age: from 1 to 18 weeks
Breed: Hybrid
Animals:
Control: 11.000 turkeys
Treatment: 11.000 turkeys
Evaluated parameters:
Weekly mortality (%)
Cumulative mortality, 10 weeks (%)
Cumulative mortality, 18 weeks (%)

Figure 4:
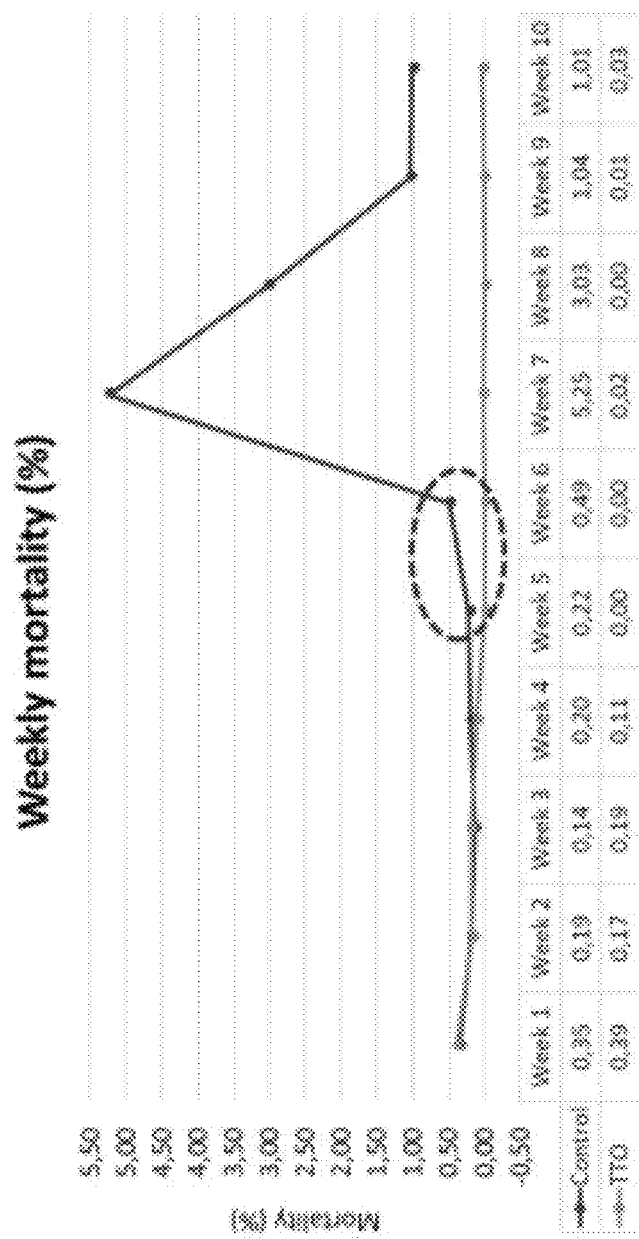
FIG. 4 is a graph illustrating the weekly mortality.
Figure 5:
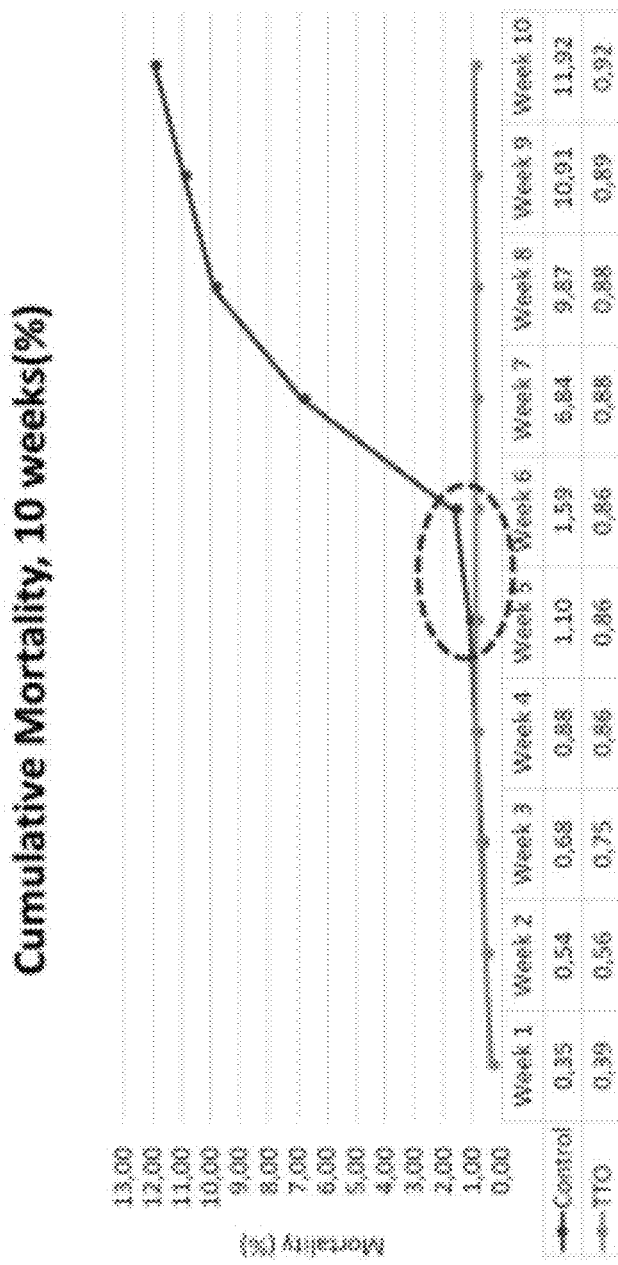
FIG. 5 is a graph showing cumulative mortality at 10 weeks.
Figure 6:
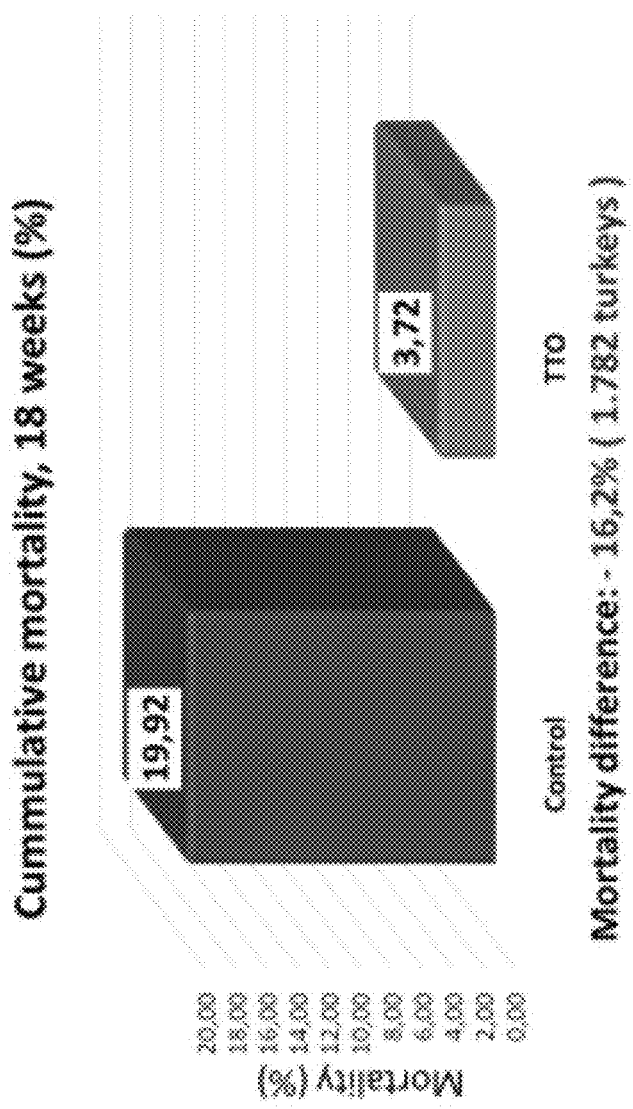
FIG. 6 is a graph showing cumulative mortality at 18 weeks.

Results:
FIG. 4 is a graph illustrating the weekly mortality.
FIG. 5 is a graph showing cumulative mortality at 10 weeks.
FIG. 6 is a graph showing cumulative mortality at 18 weeks.

Conclusions:
Effect of the administration of the present invention/Alquernat Coneb in 1-18 week-old turkeys was
a reduction of the
mortality rate in 81.3%.
No sign of histomoniasis appeared in the treatment batch.
Thanks to a better health status of the farm, the use of antimicrobials decreased.

2.3 Use of the Present Invention/Alquernat Coneb in Turkeys Against Cochlosoma, Arkansas (USA), 2017

Introduction: Cochlosoma

Cochlosoma sp. is a flagellated protozoa which has been associated with runting and catarrhal enteritis in turkey poults. Most observed cases of infestation in adults are subclinical.

The present invention/Alquernat Coneb may improve the state of the enterocytes and the local immunity of the intestine, so it can prevent problems caused by some protozoal parasites, such as Coccidia. For this reason, it may also prevent Cochlosoma infestations.

Experimental Design:
The months of November and December from 2015, 2016 and 2017 are compared in terms of flocks diagnosed positive for Cochlosoma.

Only in the year 2017 the present invention/Alquernat Coneb was administered at a dose of 1 kg/t.

The total number of flocks in the trial is 120.

Results:
Number of flocks diagnosed of Cochlosoma:

|  | Control | Control | Coneb |
| --- | --- | --- | --- |
| No flocks | 2015 | 2016 | 2017 |
| Nov. | 8 | 17 | 5 |
| Dec. | 6 | 5 | 3 |

Percentage of flocks diagnosed of Cochlosoma:

|  | Control | Control | Coneb |
| --- | --- | --- | --- |
| % flocks | 2015 | 2016 | 2017 |
| Nov. | 6.67 | 14.17 | 4.17 |
| Dec. | 5.00 | 4.17 | 2.50 |

Percentage of variation of the cases of Cochlosoma diagnosed:

| Variation rate % | 2015-2017 | 2016-2017 |
| --- | --- | --- |
| Nov. | −37.50 | −70.59 |
| Dec. | −50.00 | −40.00 |

There are important differences between 2017 and the previous years.

Figure 7:
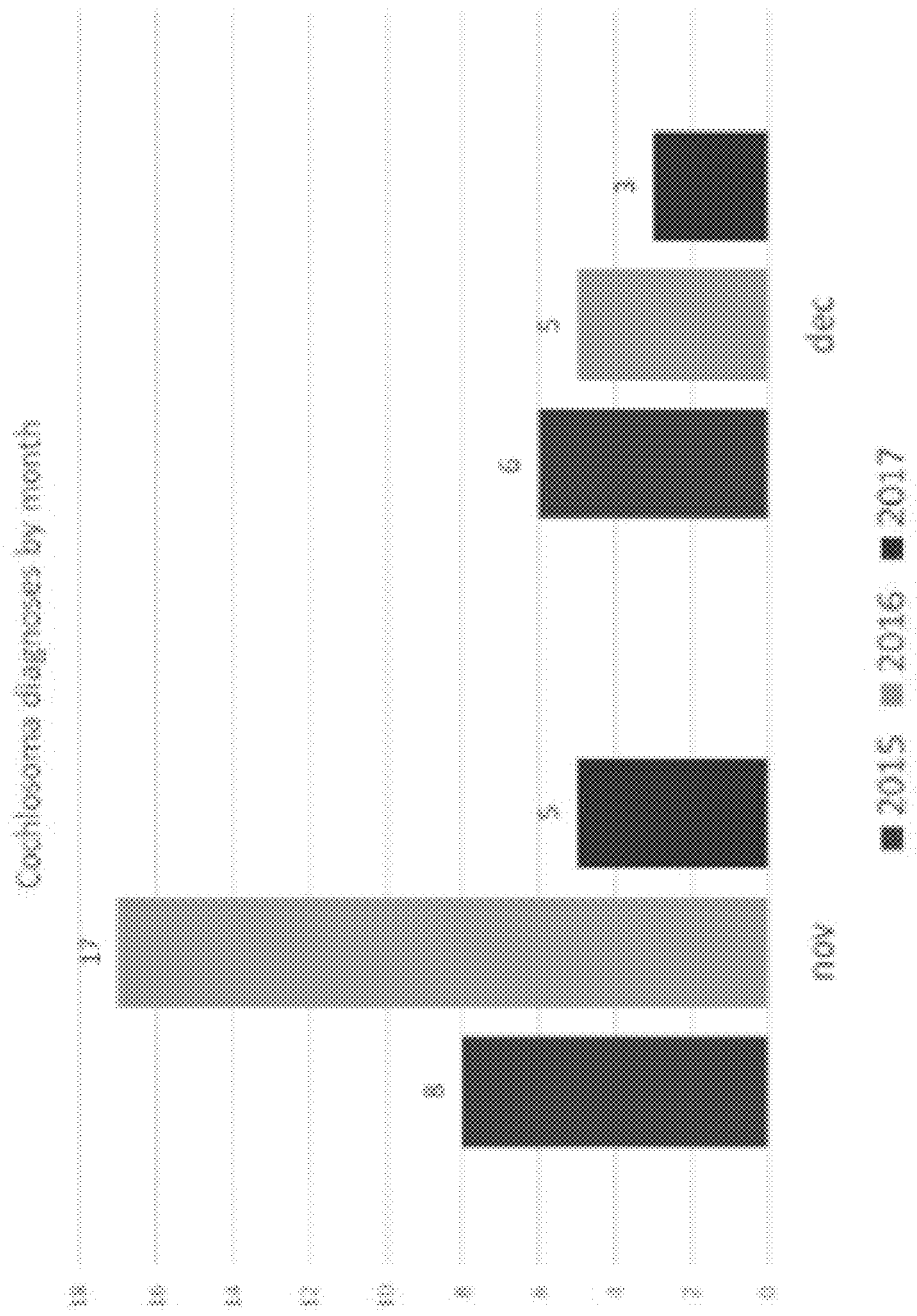
FIG. 7 is a graph illustrating *Cochlosoma* diagnoses by month.

FIG. 7 is a graph illustrating Cochlosoma diagnoses by month.

Conclusions:
There is an important reduction in Cochlosoma diagnoses between 2017 (use of the present invention/Alquernat Coneb) and the previous years.
In 2017, the minimum reduction of Cochlosoma diagnoses was 37.5%.
In 2017, the maximum reduction was 70.59%.
Adding the present invention/Alquernat Coneb in feed at a dose of 1 kg/t works as a prevention for Cochlosoma.

While the specification has been described in detail with respect to specific embodiments thereof, it will be appreciated that those skilled in the art, upon attaining an understanding of the foregoing, may readily conceive of alterations to, variations of, and equivalents to these embodiments.

What is claimed is:

1. A poultry feed product for preventing parasitic infestations comprising effective amounts of:
(a) Allium sativum extract with an alliin content of 16-17% by weight,
(b) Origanum vulgare extract with a carvacrol content of 20-22% by weight, (c) *Thymus vulgaris* extract with a cimenol content of 18-20% by weight, and (d) *Cynara scolymus* extract with a inulin content of 15-20% by weight.

* * * * *